(12) United States Patent
Carrafa

(10) Patent No.: US 10,806,340 B1
(45) Date of Patent: *Oct. 20, 2020

(54) SYSTEMS AND METHODS FOR DISPLAYING OBJECTS ON A SCREEN AT A DESIRED VISUAL ANGLE

(71) Applicant: JAND, INC., New York, NY (US)

(72) Inventor: Joseph Carrafa, Brooklyn, NY (US)

(73) Assignee: JAND, Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/394,088

(22) Filed: Apr. 25, 2019

Related U.S. Application Data

(60) Division of application No. 15/586,552, filed on May 4, 2017, now Pat. No. 10,314,475, which is a
(Continued)

(51) Int. Cl.
| | | |
|---|---|---|
| *A61B 3/02* | (2006.01) | |
| *A61B 3/00* | (2006.01) | |
| *G06T 3/20* | (2006.01) | |
| *H04N 7/18* | (2006.01) | |
| *A61B 3/032* | (2006.01) | |

(Continued)

(52) U.S. Cl.
CPC .......... *A61B 3/0041* (2013.01); *A61B 3/0025* (2013.01); *A61B 3/0091* (2013.01); *A61B 3/032* (2013.01); *G06T 3/20* (2013.01); *H04M 1/72522* (2013.01); *H04N 7/18* (2013.01); *H04N 7/183* (2013.01); *H04M 1/2755* (2013.01); *H04M 2250/52* (2013.01); *H04N 5/253* (2013.01)

(58) Field of Classification Search
CPC ......... A61B 3/032; A61B 3/0033; A61B 3/18; A61B 3/024; A61B 3/028
USPC ....................................................... 351/223
See application file for complete search history.

(56) References Cited

U.S. PATENT DOCUMENTS

| | | |
|---|---|---|
| 5,877,841 A | 3/1999 | Jeon |
| 5,946,075 A | 8/1999 | Horn |

(Continued)

FOREIGN PATENT DOCUMENTS

| | | |
|---|---|---|
| EP | 3402384 | 11/2018 |
| WO | 2013126989 | 9/2013 |

(Continued)

OTHER PUBLICATIONS

Examination Report for Canadian App. No. 2995458, dated Dec. 21, 2018, 3 pages.

(Continued)

*Primary Examiner* — Mohammed A Hasan
(74) *Attorney, Agent, or Firm* — Duane Morris LLP

(57) ABSTRACT

A server in communication with a first device capable of receiving input from a camera attached to the first device, and a second device capable of displaying output, is provided. The server is configured to receive, from the first device, data relating to characteristics of the camera and characteristics of an image obtained by the camera of a screen of the second device; determine a screen pixel length of the screen; and provide instructions to the second device to display on the screen an object at a desired visual angle in response to the data received from the second device and the screen pixel length, while the first device is positioned at an arbitrary distance from the screen.

18 Claims, 6 Drawing Sheets

Related U.S. Application Data continuation of application No. 14/867,677, filed on Sep. 28, 2015, now Pat. No. 9,770,165, which is a continuation of application No. 14/825,342, filed on Aug. 13, 2015, now abandoned.

(51) Int. Cl.
*H04M 1/725* (2006.01)
*H04M 1/2755* (2006.01)
*H04N 5/253* (2006.01)

(56) References Cited

U.S. PATENT DOCUMENTS

| | | | |
|---|---|---|---|
| 6,238,049 | B1 | 5/2001 | Griffin et al. |
| 6,386,707 | B1 | 5/2002 | Pellicano |
| 6,556,131 | B1 | 4/2003 | Besharat et al. |
| 6,578,966 | B2 | 6/2003 | Fink et al. |
| 7,222,091 | B2 | 5/2007 | Yoshida |
| 7,267,439 | B2 | 9/2007 | Toshima et al. |
| 7,367,675 | B2 | 5/2008 | Maddalena et al. |
| 7,374,285 | B2 | 5/2008 | Toshima et al. |
| 7,415,212 | B2 | 8/2008 | Matsushita et al. |
| 7,429,109 | B2 | 9/2008 | Toshima et al. |
| 7,819,524 | B2 | 10/2010 | Kanazawa et al. |
| 8,066,376 | B2 | 11/2011 | Wang et al. |
| 8,083,353 | B2 | 12/2011 | Hytowitz |
| 8,322,857 | B2 | 12/2012 | Barbur et al. |
| 8,740,386 | B2 | 6/2014 | Foster |
| 8,757,805 | B2 | 6/2014 | Hytowitz |
| 8,783,871 | B2 | 7/2014 | Pamplona et al. |
| 8,786,707 | B1 | 7/2014 | Ettinger |
| 9,033,508 | B2 | 5/2015 | Bartlett et al. |
| 9,055,904 | B2 | 6/2015 | Yoo et al. |
| 9,066,683 | B2 | 6/2015 | Zhou |
| 9,230,062 | B2 | 1/2016 | Seriani |
| 9,236,024 | B2 | 1/2016 | Coon |
| 9,237,842 | B2 | 1/2016 | Lee et al. |
| 9,237,846 | B2 | 1/2016 | Mowrey et al. |
| 9,314,154 | B2 | 4/2016 | Palanker et al. |
| 9,549,669 | B2 | 1/2017 | Limon |
| 9,770,165 | B2 * | 9/2017 | Carrafa ................ A61B 3/0041 |
| 2005/0200784 | A1 * | 9/2005 | Kume ................ G02F 1/133555 |
| | | | 349/130 |
| 2008/0189173 | A1 | 8/2008 | Bakar et al. |
| 2012/0050685 | A1 | 3/2012 | Bartlett et al. |
| 2012/0050686 | A1 | 3/2012 | Bartlett et al. |
| 2012/0069179 | A1 | 3/2012 | Gish |
| 2012/0069199 | A1 | 3/2012 | Chang et al. |
| 2012/0212706 | A1 | 8/2012 | Chou et al. |
| 2012/0253201 | A1 * | 10/2012 | Reinhold ............... A61B 5/1113 |
| | | | 600/473 |
| 2012/0324123 | A1 | 12/2012 | Fox et al. |
| 2012/0327123 | A1 | 12/2012 | Felt |
| 2013/0026217 | A1 | 1/2013 | Boudville |
| 2013/0091302 | A1 * | 4/2013 | Roscheisen ........ H04N 1/00307 |
| | | | 709/237 |
| 2013/0141697 | A1 | 6/2013 | Berry |
| 2013/0271478 | A1 | 10/2013 | Lazzaro et al. |
| 2014/0268060 | A1 | 9/2014 | Lee et al. |
| 2014/0293228 | A1 | 10/2014 | Hytowitz |
| 2015/0055085 | A1 | 2/2015 | Fonte |
| 2015/0070650 | A1 | 3/2015 | Seriani |
| 2015/0098060 | A1 | 4/2015 | Zhou |
| 2015/0164318 | A1 | 6/2015 | Zhou |
| 2016/0035122 | A1 | 2/2016 | Stewart et al. |
| 2016/0066780 | A1 | 3/2016 | Pamplona et al. |
| 2016/0098528 | A1 | 4/2016 | Seriani |
| 2016/0128560 | A1 | 5/2016 | Lee et al. |
| 2016/0128567 | A1 | 5/2016 | Lee et al. |
| 2016/0157711 | A1 | 6/2016 | Maddalena et al. |
| 2016/0157716 | A1 | 6/2016 | Pamplona et al. |
| 2016/0234477 | A1 | 8/2016 | Singhal |
| 2017/0079523 | A1 | 3/2017 | Limon |

FOREIGN PATENT DOCUMENTS

| | | |
|---|---|---|
| WO | 2014064719 | 5/2014 |
| WO | 2015148442 | 10/2015 |
| WO | 2016046186 | 3/2016 |
| WO | 2016084086 | 6/2016 |
| WO | 2016181308 A1 | 11/2016 |
| WO | 2016181309 A1 | 11/2016 |
| WO | 2016181310 A1 | 11/2016 |

OTHER PUBLICATIONS

Non-Final Office Action for U.S. Appl. No. 15/586,552, dated Oct. 2, 2018, 10 pages.

Australian Examination Report No. 1 for Application No. 2016306656, dated May 10, 2018, 3 pages.

International Search Report and the Written Opinion of the International Searching Authority from corresponding PCT/US2016/46718 dated Oct. 21, 2016.

Zhang, "A Flexible New Technique for Camera Calibration," IEEE Transactions on Pattern Analysis and Machine Intelligence, 22(11):1330-1334, 2000.

Supplementary Extended Search Report for EP App. No. 16835966.9, dated Feb. 26, 2019, 10 pages.

Examination Report dated Apr. 20, 2020 in corresponding Australian Application No. 2019203786.

* cited by examiner

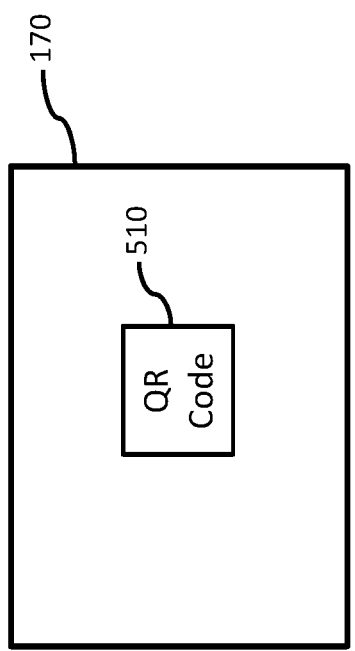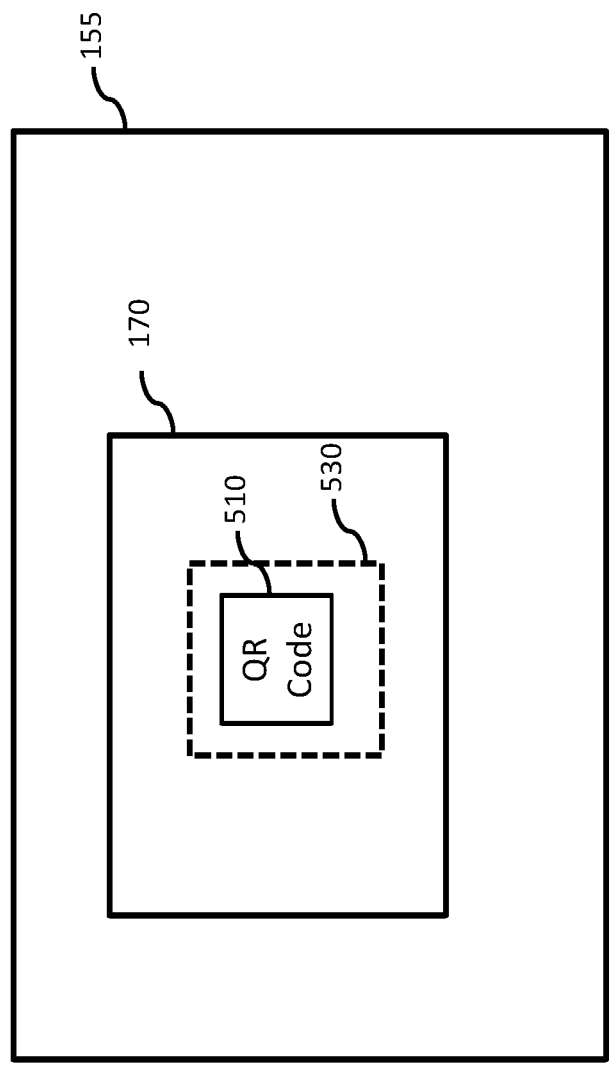

SYSTEMS AND METHODS FOR DISPLAYING OBJECTS ON A SCREEN AT A DESIRED VISUAL ANGLE

CROSS-REFERENCE TO RELATED APPLICATION

This application is a Divisional of, and claims priority to, U.S. patent application Ser. No. 15/586,552, filed on May 4, 2017, which is a Continuation of U.S. patent application Ser. No. 14/867,677, filed on Sep. 28, 2015 and which issued as U.S. Pat. No. 9,770,165 on Sep. 26, 2017, which is a Continuation-in-Part of U.S. patent application Ser. No. 14/825,342, filed on Aug. 13, 2015 and now abandoned, the entire content of each of which are incorporated herein by reference in their entirety for all purposes.

BACKGROUND

Technical Field

The technical field generally relates to displaying objects on a screen at a desired visual angle, and more particularly, in one aspect, to systems and methods for displaying optotypes during an eye examination.

Background Discussion

Eye examinations are routinely used to determine the appropriate lens prescription or make other diagnoses for patients. Eye exams have traditionally been performed by optometrists or the like in an office where the test subject is positioned at a set distance from an eye chart displaying optotypes of a known size. The test administrator is able to calculate the perceived size of the optotypes from the perspective of the test subject, and draw conclusions regarding the subject's vision according to the test results. Efforts to translate eye exam procedures from a doctor or technician's office to non-traditional locations such as self-administered tests at home are hampered by the difficulties associated with ascertaining the perceived size of the characters used in the test. Previously proposed solutions such as using measuring tape or counting steps to determine a distance from a computer screen displaying an eye test require additional equipment or steps and may erode a user's confidence in the results, making a test administered out of office less attractive.

SUMMARY

According to one aspect, a server in communication with a first device capable of receiving input from a camera attached to the first device, and a second device capable of displaying output, is provided. The server is configured to receive, from the first device, data relating to characteristics of the camera and characteristics of an image obtained by the camera of a screen of the second device; determine a screen pixel length of the screen; and provide instructions to the second device to display on the screen an object at a desired visual angle in response to the data received from the second device and the screen pixel length, while the first device is positioned at an arbitrary distance from the screen.

According to one embodiment, the server is further configured to pair the first device to the second device. According to another embodiment, the server is further configured to receive from the second device an indication of the screen pixel length of the screen.

According to yet another embodiment, the data associated with characteristics of the camera comprise a focal length and a sensor size of the camera. According to a further embodiment, the data associated with characteristics of the image of the screen include a camera pixel height of the image and a camera pixel height of the screen within the image. According to a still further embodiment, the server is further configured to determine a visual angle of the screen prior to providing instructions to the second device to display the object.

According to one embodiment, the displayed object is an optotype, and the server is further configured to receive an indication from either the first device or the second device from a test subject proximate to the first device in response to the displayed optotype. According to a further embodiment, the server is further configured to determine, based at least in part on the indication provided by the test subject in response to the displayed optotype, at least one of a diagnosis for the test subject, a lens prescription for the test subject, and information to be provided to a doctor to determine a diagnosis or a lens prescription for the test subject.

According to another aspect, a process for conducting a vision test includes obtaining an image of a screen using a camera of a mobile device; determining a camera pixel length of the screen in the image; determining a desired screen pixel dimension of an object to be displayed on the screen to produce a desired visual angle for the object; and causing the object to be displayed on the screen at the desired visual angle.

According to one embodiment, the object is an optotype, the method further including receiving an indication from a test subject in response to the optotype. According to a further embodiment, the process includes determining at least one characteristic of the test subject's vision based at least in part on the received indication. According to a still further embodiment, the at least one characteristic is at least one of a diagnosis and a lens prescription for the test subject. According to a further embodiment, the process includes transmitting from the mobile device to a server the indication from the test subject in response to the optotype.

According to another embodiment, obtaining the image of the screen occurs at an arbitrary distance from the screen.

According to one embodiment, the process includes pairing the mobile device with a computer associated with the screen. According to a further embodiment, the process includes transmitting data from the mobile device to a server, the data representing at least one characteristic of the camera of the mobile device and at least one characteristic of the image of the screen of the computer.

According to another embodiment, the at least one characteristic of the image of the screen of the computer includes a first camera pixel dimension of the image and a second camera pixel dimension of the screen within the image.

According to yet another aspect, a process of operating a mobile device includes obtaining an image of a computer screen using a camera of the mobile device; determining a camera pixel length of the computer screen in the image; determining a desired screen pixel length of an object to be displayed on the computer screen to produce a desired visual angle for the object; and receiving an indication from a test subject in response to the object displayed on the computer screen.

According to one embodiment, the process includes pairing the mobile device with the computer associated with the computer screen. According to another embodiment, the process includes determining at least one characteristic of the user's vision based at least in part on the received indication.

Still other aspects, embodiments, and advantages of these exemplary aspects and embodiments, are discussed in detail below. Moreover, it is to be understood that both the foregoing information and the following detailed description are merely illustrative examples of various aspects and embodiments, and are intended to provide an overview or framework for understanding the nature and character of the claimed subject matter. Particular references to examples and embodiments, such as "an embodiment," "an example," "one example," "another embodiment," "another example," "some embodiments," "some examples," "other embodiments," "an alternate embodiment," "various embodiments," "one embodiment," "at least one embodiments," "this and other embodiments" or the like, are not necessarily mutually exclusive and are intended to indicate that a particular feature, structure, or characteristic described in connection with the embodiment or example and may be included in that embodiment or example and other embodiments or examples. The appearances of such terms herein are not necessarily all referring to the same embodiment or example.

Furthermore, in the event of inconsistent usages of terms between this document and documents incorporated herein by reference, the term usage in the incorporated references is supplementary to that of this document; for irreconcilable inconsistencies, the term usage in this document controls. In addition, the accompanying drawings are included to provide illustration and a further understanding of the various aspects and embodiments, and are incorporated in and constitute a part of this specification. The drawings, together with the remainder of the specification, serve to explain principles and operations of the described and claimed aspects and embodiments.

BRIEF DESCRIPTION OF DRAWINGS

Various aspects of at least one embodiment are discussed below with reference to the accompanying figures, which are not intended to be drawn to scale. The figures are included to provide an illustration and a further understanding of the various aspects and embodiments, and are incorporated in and constitute a part of this specification, but are not intended as a definition of the limits of any particular embodiment. The drawings, together with the remainder of the specification, serve to explain principles and operations of the described and claimed aspects and embodiments. In the figures, each identical or nearly identical component that is illustrated in various figures is represented by a like numeral. For purposes of clarity, not every component may be labeled in every figure. In the figures:

FIGS. 4A and 4B are illustrations of a user interface during a device pairing step according to one or more embodiments;

DETAILED DESCRIPTION

Figure 1:
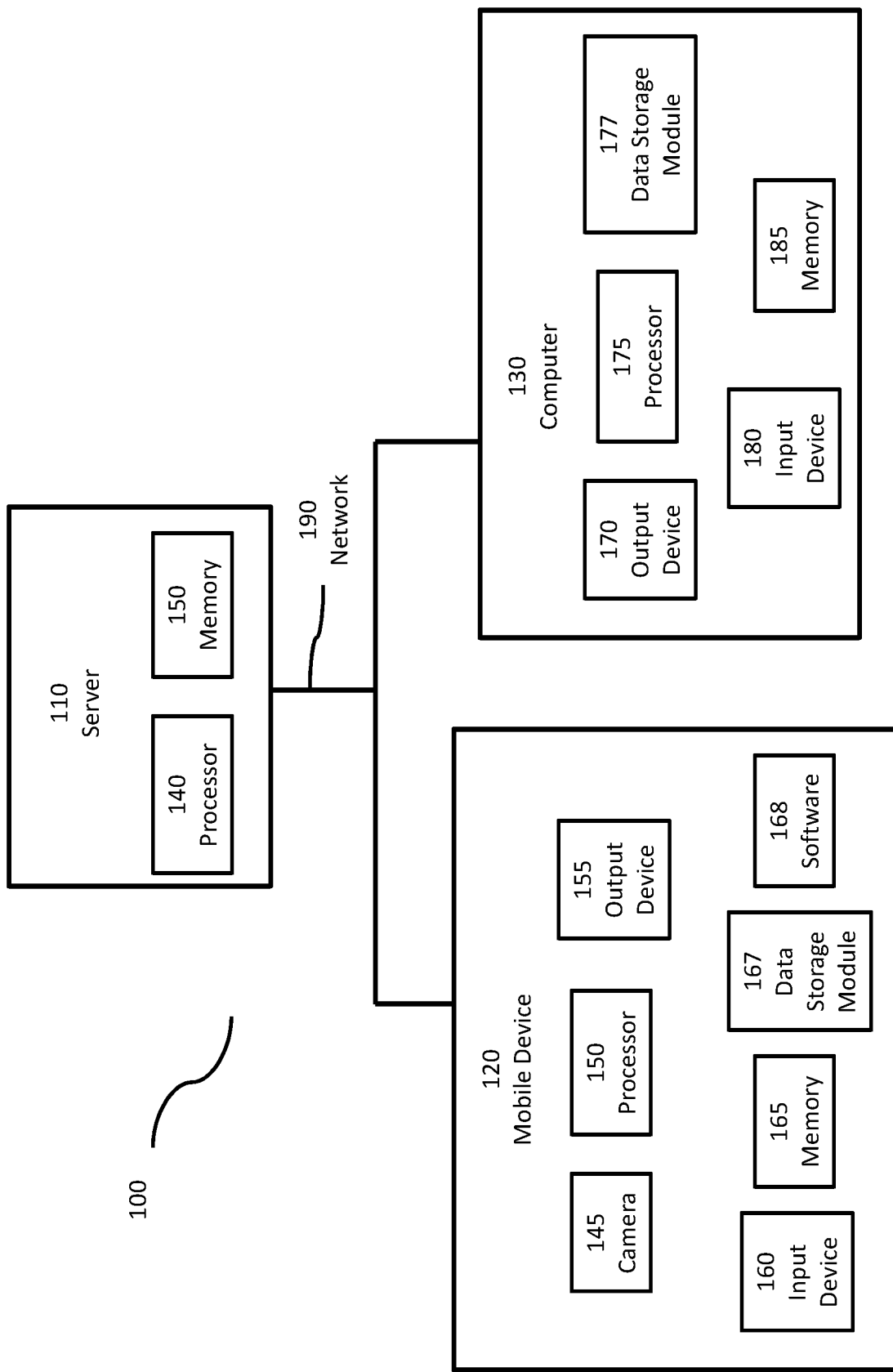
FIG. 1 is a block diagram of a system according to one or more embodiments.

According to one or more embodiments, the methods and systems disclosed provide for the display of objects on a screen so that they are perceived at a desired visual angle by a user positioned at an arbitrary distance from the screen. A visual angle may be understood as the angle along a given plane occupied by an object in a viewer's field of sight. For example, a second object twice as big but also twice as distant from a viewer as a first object will have about the same visual angle as the first object.

According to one or more embodiments, the methods and systems disclosed allow for performing a web-based process that uses a camera on a mobile device, such as a smartphone, tablet, etc., in communication with a computer screen, such as one for a desktop computer, a laptop computer, a tablet, etc., to present an object at a desired visual angle in, for example, units of arcminutes on the computer screen, regardless of the exact distance the user is from the screen. According to one application, this method allows the user to perform an eye examination without calibrating the screen to determine the physical size of objects displayed on it, and without requiring the subject be at a particular distance from the screen. While the term "camera" is used throughout the specification, it should be understood that other light sensors capable of performing analogous functions are also understood to be within the scope of the disclosed invention.

Conventionally, when determining visual acuity during a typical eye examination, the distance the subject is from the test is used to determine the physical size of the optotypes presented so as to achieve a desired visual angle for the displayed objects, i.e., the desired angle at which the object is to be perceived. For example, at 3 meters, a person with 20/20 vision can read a standard "E" that is 4.36 mm tall on a Snellen chart, while at 6 meters, that letter at 8.73 mm tall would appear to be the same size, and would also be legible to a person with 20/20 vision. The two letters look the same because the angle at which they hit the eye is the same. This angle may be referred to as the visual angle. Because of this, visual acuity is often described using the "minimum angle of resolution" (MAR). For example, a person with 20/20 vision has an MAR of 1 minute of arc, or $\frac{1}{60}$ of a degree.

In at least some embodiments directed to performing an eye examination, the desired visual angle of an optotype can be displayed without needing to know either the exact distance of the test subject to the screen or the physical letter size displayed on the screen for the examination. The subject, or user, may instead stand at an arbitrary distance, i.e., a distance within a range in which the performed method can be carried out successfully for a given camera pixel resolution or the requirements of the particular application, e.g., eye examination, but a distance that need not be pre-determined or exact. Also, the exact physical height of the displayed objects on the screen does not need to be known in units of physical length such as centimeters or inches. By eliminating the need for these two conventional requirements, the process for displaying objects is simplified and the reliability of the results is increased.

According to one or more embodiments, the methods provided may facilitate a user to undergo an eye examination without the need for technical or trained personnel to administer the test. As such, this disclosure opens up the potential for a range of people to receive an accurate eye examination who may have difficulty accessing an optician's office (those that are infirm, remote, etc.), or those who may prefer the convenience of self-administering an examination.

According to one or more embodiments, the disclosed methods and systems are implemented using a camera capable of running custom software and, according to some examples, displaying feedback to the user (such as may be provided by a smartphone or other mobile or portable device, such as a tablet or laptop computer). According to one or more embodiments, the methods provided can be run on most consumer mobile devices or any portable computing device that includes a camera.

The mobile device can be paired, or linked, to a web page or application running on a computer such that the mobile device can be used to control the application on the computer. This can be helpful for guiding the user through the object display process and also for guiding the user through an eye examination.

Turning to the figures, FIG. 1 illustrates a block diagram of a system 100 according to one or more embodiments. In the embodiment shown in FIG. 1, the system 100 comprises a server 110 in communication with a first device 120 and a second device 130. As shown, the first device 120 is coupled to, and can exchange data with the server 110 and the computing device 130 via the network 190. In addition, according to this example, the first device 120 includes a camera 145, a processor 150 coupled to the camera, an output device 155, such as a monitor or display screen or audio speaker, an input device 160, such as a touch surface, a keyboard, microphone, or a mouse, a data storage module 167, and a memory 165 coupled to the processor 150. The first device 120 also includes eye examination software 168.

The server 110 includes one or more computing devices located remote or local to the first and second devices 120 and 130. The server includes a processor 140 and a memory 142 coupled to the processor. In one example, the memory 142 includes volatile memory, such as RAM, and non-volatile memory, such as a magnetic disk.

The second device 130 is coupled to, and can exchange data with, the server 110 and the mobile device 120 via the network 190. In addition, according to this example, the second device 130 includes the processor 175, a data storage module 177, a memory 185 coupled to the processor 175, an output device 170, such as a monitor or display screen or audio speaker, and an input device 180, such as a touch surface, a keyboard, microphone, or a mouse.

The first device 120 is a portable computing device. For example, it may be a mobile device, such as a smart phone, tablet, or laptop computer, all of which are encompassed by the terms "portable computing device" or "mobile device." The mobile device 120 is capable of delivering and/or receiving data to or from server 110. The second device 130 may be a portable computing device, like any of those described for the first device 120, or a stationary computing device. Unless specified otherwise, the terms "monitor" or "screen" may be understood to encompass any visual display associated with a portable or stationary computing device.

The server 110 exchanges data with the first and second devices 120 and 130. This data may be exchanged through an installed program in the first or second device 120 or 130, or through a web page loaded on the first or second device 120 or 130.

In use, the first and second devices 120 and 130 may be used in conjunction to display objects at a desired visual angle. The output display 170 of the second device 130 may be used to display any required pattern, a substantially blank screen, and/or eye examination material. The images displayed on the monitor 170 may be provided to the monitor 170 by the server 110 in response to instructions received from the server 110, and the particular instructions provided to the monitor 170 may be based on information received from the camera device 120. A pairing of the first and second devices 120 and 130, as further discussed below, may facilitate their coordination.

The computing device 130, as shown in FIG. 1, is internet-enabled and the various patterns, images, or testing material displayed is provided through a web-page, in response to output from the first device 120. In alternative embodiments, an application or program running on the computer 130 is responsible for the content displayed.

While in the system 100 shown in FIG. 1 both the first device 120 and the second device 130 are in communication with the server 110, alternative configurations are also considered within the scope of the present disclosure. For example, according to certain embodiments the device 120 including the camera 145 and/or the second device 130 may not be in communication with a server 110 or each other. For example, all the instructions required by the camera device 120 may already be stored on the device 120. Likewise, information or instructions for what to display on the second device 130 may be provided without requiring communication over a network. Also, the second device 130 may be in direct communication with the first device 120 using one of a number of known wireless protocols.

According to one or more embodiments, a system like that shown in FIG. 1 is implemented in processes directed to displaying objects at a desired visual angle from the perspective of the user. These objects may be used in a variety of applications, including a self-administered eye examination. In the context of an eye examination, the desired visual angle is determined according to the requirements of the test and the visual angle of the optotypes presented may be pre-determined according to a pre-set routine or determined dynamically in response to feedback from a test subject over the course of the examination. For example, if a test subject indicates that he/she cannot perceive an object presented at one visual angle, the system may account for that response and follow by presenting an optotype at a larger visual angle. The objects presented may be static (unmoving) or dynamic (moving and/or changing).

Figure 2:
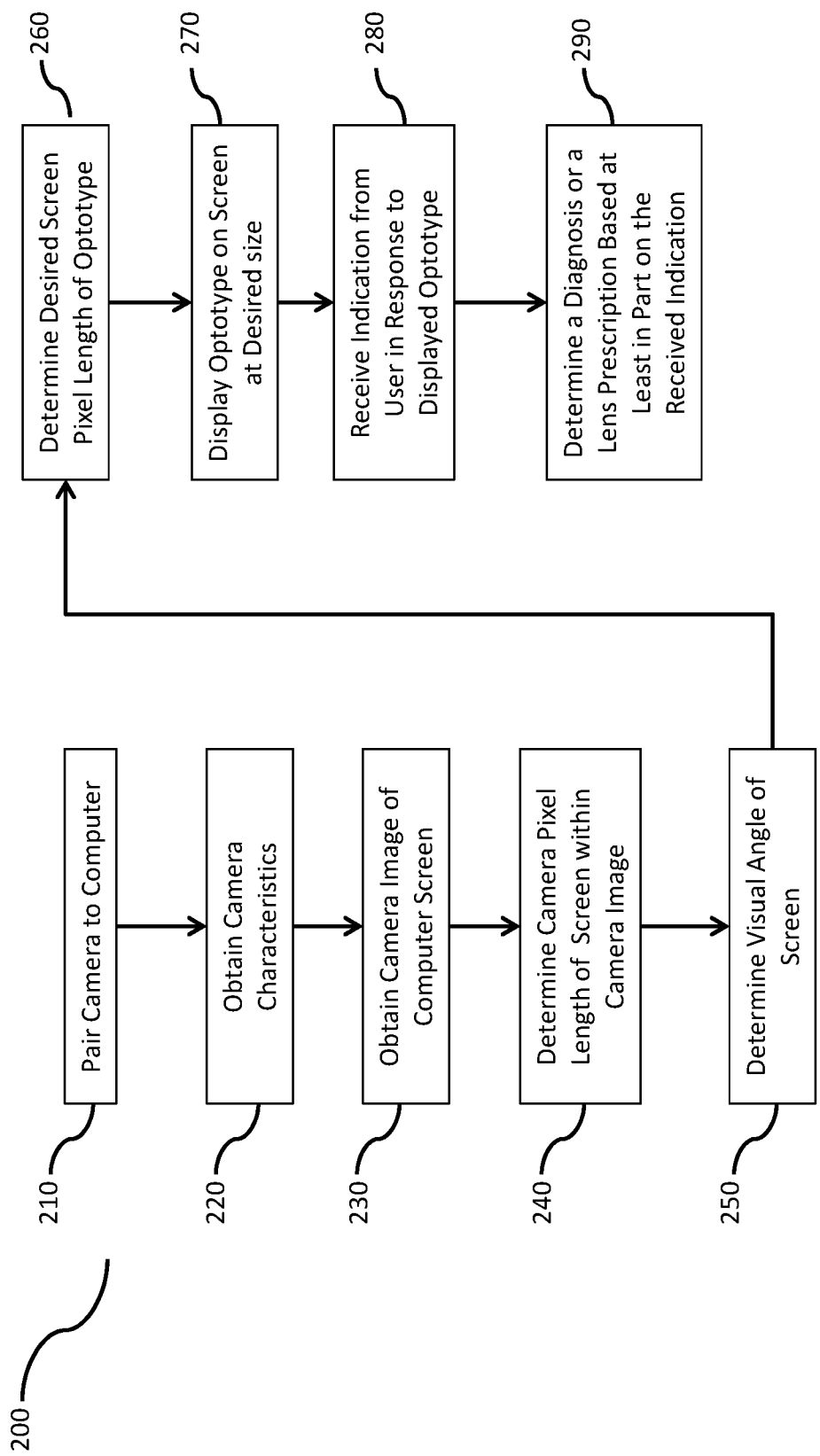
FIG. 2 is a flow chart of a process according to one or more embodiments.

FIG. 2 is a flow chart of a process 200 for displaying objects on a screen 170 at a desired visual angle for a user positioned proximate to, including holding, the mobile device 120. These objects may optionally comprise optotypes and be used in determining a diagnosis or lens prescription according to one or more embodiments. One or more embodiments of the process 200 may be implemented using a system like that shown in FIG. 1. While several steps are shown in FIG. 2 it is to be understood that some of these steps are optional, and the implementation of a process without these optional steps is still considered within the scope of the presently disclosed invention.

A first step 210 of the process 200 includes pairing the camera of the portable device 120 with the computer 130. The step of pairing facilitates the coordination of instructions and information between the portable device 120 and the computer 130. Once paired, the server 110 may deliver instructions to the computer 130 directing what images are displayed on its monitor 170 in response to information received from the camera 145 of the device 120. The step of pairing may be achieved by any technique known to one of ordinary skill in the art that will allow the server 110 to associate the portable device 120 with the computer 130. For example, an identifier may be displayed on the monitor 170 of computer 130 and captured by the camera of device 120 or vice versa. In some embodiments a QR code is displayed on the monitor 170. The camera then captures an image of the code and transmits it to the server 110, allowing the server 110 to match the two devices 120 and 130 and coordinate the instructions sent to each.

FIGS. 4A and 4B illustrate user interfaces during a device pairing step according to one or more embodiments. In FIG. 4A the monitor 170 of the computer 130 displays a QR code 510. In FIG. 4B the output display 155 of the camera 145 displays the monitor 170 with the QR code 510. The code 510 is positioned within the target box 530 of the output display 155. The code is identified and the two devices 120 and 130 are paired so that output and input between the two devices 120 and 130 may be coordinated. In one embodiment, the QR code may be generated by the server 110 and provided to the device 130, while in other embodiments, the device 130 may generate the QR code and provide it to the server 110. In other embodiments, images other than QR codes may be used to pair the devices, and other identifiers may also be used. For example, a string of letters and or numbers can be displayed on one of devices 120 and 130, and entered in the other of the devices 120 and 130 to pair the devices.

Step 220 of the process 200 includes obtaining camera characteristics for calculations conducted in later steps in the process. According to certain embodiments, these camera characteristics include the focal length of the camera and the physical size of the sensor. According to some embodiments, any process for calibrating a camera 145 known to a person of ordinary skill in the art may be utilized to obtain these parameters. In other embodiments, the characteristics of the camera 145 may be known, for example, based on the model of the mobile device 120 used, and calibration of the camera 145 may not be necessary. Parameters of the camera used in performing the disclosed methods, such as focal length and physical size of the sensor (or the value of their ratio), may be obtained directly from the camera or may be retrieved, such as from a database. Alternatively, these parameters may be determined through an optional calibration process, like that described in U.S. patent application Ser. No. 14/732,435, titled, "SYSTEM AND METHOD FOR DETERMINING DISTANCES FROM AN OBJECT," and incorporated herein by reference in its entirety and for all purposes.

Step 230 of the process 200 includes obtaining an image of a display screen 170 of the computer 130 using the camera 145 of the portable device 120. This image may be obtained by positioning the device 120 so that the screen 170 is within its output display 155.

Figure 5A:
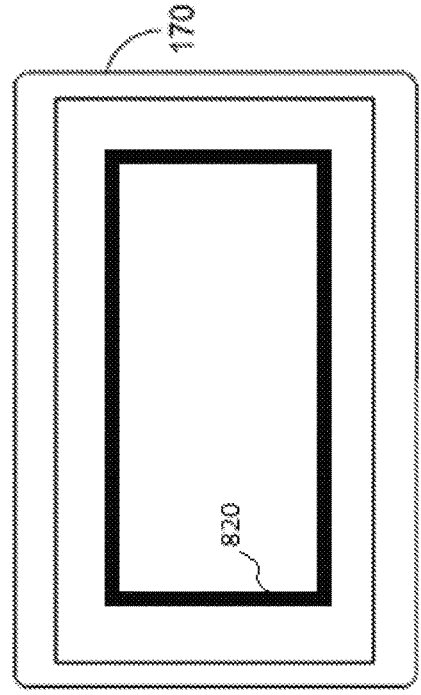
FIGS. 5A, 5B, and 5C are illustrations of user interfaces during a process step according to one or more embodiments.
Figure 5B:
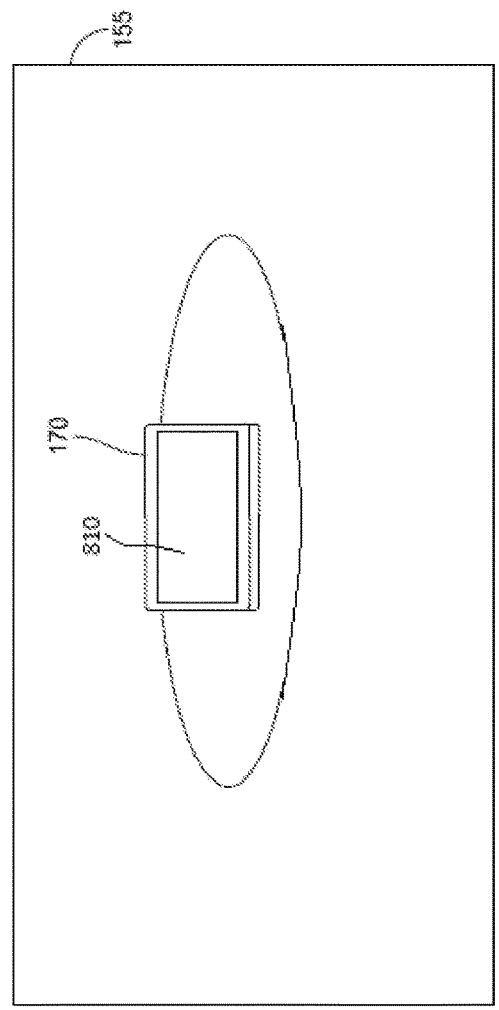
Figure 5C:
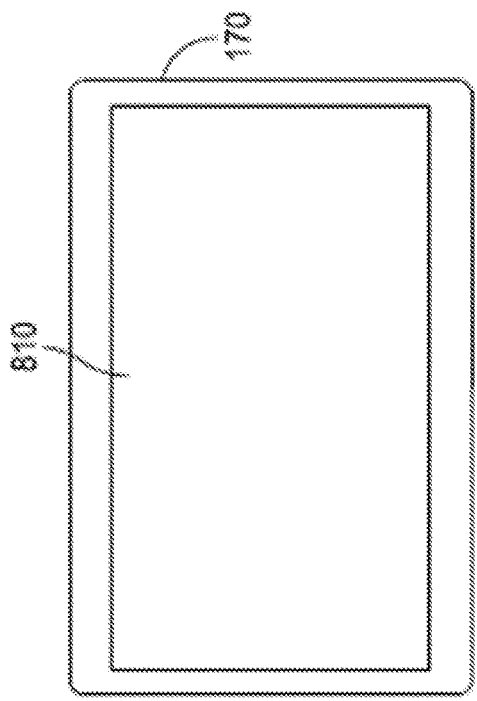

Step 230 is illustrated in FIGS. 5A, 5B, and 5C. FIG. 5A illustrates a monitor screen 170, which is paired with the camera device 120, displaying a white image 810 (to aid in contrasting with the background). FIG. 5B illustrates a display 155 on the camera device 120, within which the screen 170 is displayed. In an alternative embodiment, a target 830 is defined within the screen 170. The target 830 may be any shape or pattern that aids in distinguishing itself from the surrounding environment so that the target area may be more easily detected. In FIG. 5C the target 830 is defined by a black box with a white interior.

Figure 3:
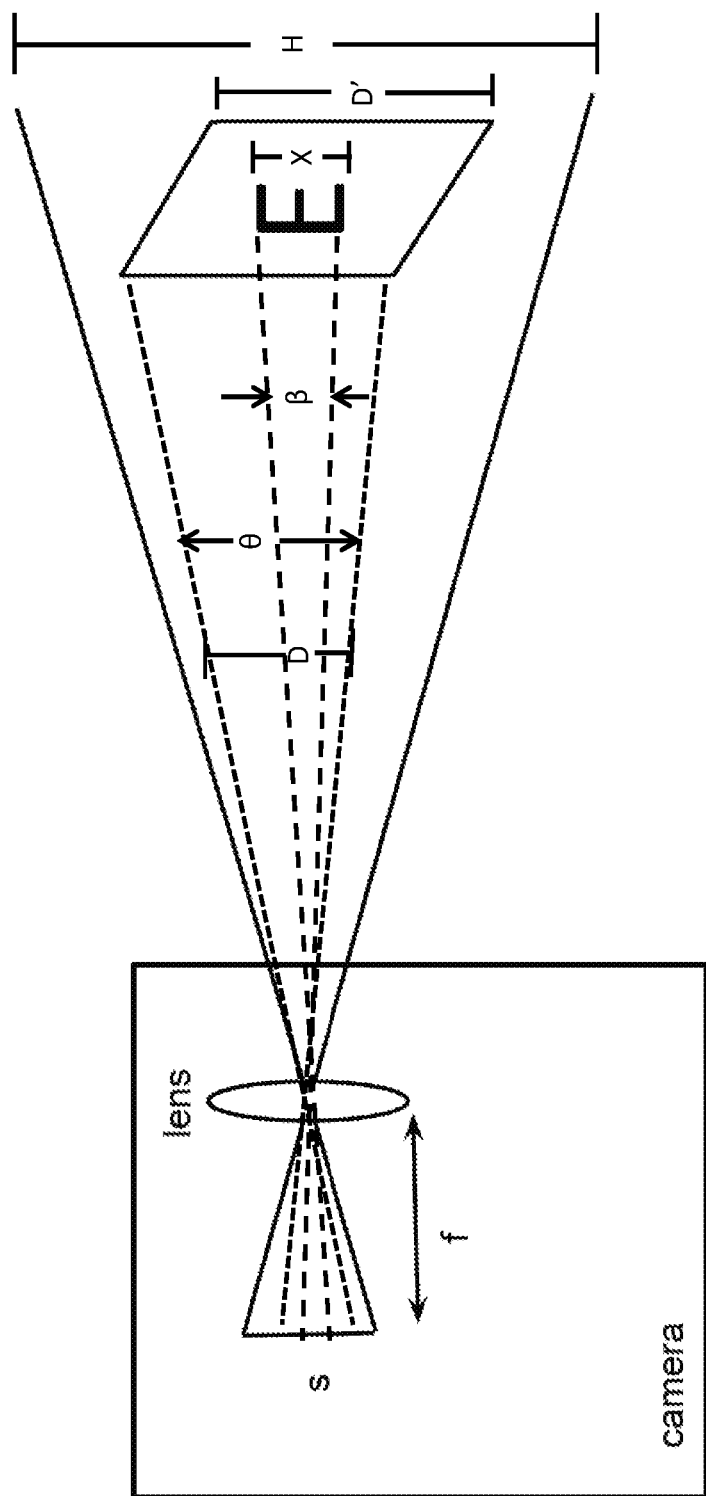
FIG. 3 is a diagram of variables used in performing a process according to one or more embodiments.

Step 240 of the process 200 includes determining a camera pixel length of the screen 170 that was captured in the camera image. Preferably, the screen contrasts with the background to facilitate this step 240, as shown in FIGS. 5A, 5B, and 5C. The image is processed to determine the length of one or more dimensions of the screen in units of camera pixels. Referring to FIG. 3, the length of the screen 170 in camera pixels is shown as D. This length may be referred to as camera pixel length or image pixel length. In this context, the use of the term "screen" may be understood to include the entire screen or a designated portion of the screen, such as the target portion 830, shown in FIG. 5C, for example, unless stated otherwise.

Having determined the camera pixel length of the screen 170, on which the object is to be displayed, the following two steps 250 and 260 together determine the screen pixel size, X, of the object 310 necessary for it to appear at a desired visual angle, β, to a user.

Step 250 includes determining the visual angle of the screen 170 from the perspective of a user near the mobile device 120. Referring to FIG. 3, the angle of the entire field of view of the image is a function of the ratio of the size of the camera sensor, S, and the focal length, F—the larger the sensor, S, the wider the camera angle. The visual angle of the screen 170 (referred to in FIG. 3 as θ) can be understood as a fraction of the angle of the entire field of view. Referring to FIG. 3, H is the camera pixel height of the entire image, while D, determined in step 240, is the camera pixel height of the screen 170. The ratio of D to H and the ratio of S to F can together be used to relate these values to a visual angle, θ, of the screen, according to the formula shown in Equation (1):

$$\theta = 2*\tan^{-1}\left(\frac{D*S}{2*H*F}\right) \quad (1)$$

Once D is determined through step 240, all of the variables necessary to determine the visual angle, θ, of the computer screen 170 are known. The image has a known height, H (again in units of camera pixels). Likewise, the physical sizes of the sensor, S, and the focal length, F, or at least their relevant ratio of S to F, are known, as discussed above with reference to step 220.

Step 260 of the process 200 includes determining a screen pixel length for the object 310 that is to be displayed on the screen 170, a value referred to in FIG. 3 as X. This value may be determined in units of screen pixels (screen pixel length). An object having this length will appear at the desired visual angle to a user. This step is understood to include determining the screen pixel length of the various components of the object, so that the components of the object are re-sized proportionally, and the resulting object maintains its correct shape. X is a function of the known values, according to the formula shown in Equation (2):

$$X = D'*\frac{\tan\left(\frac{\beta}{2}\right)}{\tan\left(\frac{\theta}{2}\right)} \quad (2)$$

Wherein:
D' is the length of the screen in units of screen pixels, a value which can be obtained directly from the computer 130;
Θ is the visual angle of the computer screen 170; and
β is the desired visual angle for the object 310, which if it is an optotype in an eye examination, is determined according to the requirements of the eye examination.

Alternatively, where the distance from the screen is very large compared to the height of the object to be displayed, the ratio of the visual angle, β, of the object 310 to the visual angle, Θ, of the screen 170 is approximately proportional to the ratio of the height of the object 310, X, to the height of the screen 170, D'. Therefore, the object display height, X, can be approximated according to the formula shown in Equation (3):

$$X = D' * \left(\frac{\beta}{\theta}\right) \quad (3)$$

Once the value for X is determined, it can then be inserted into a command to produce on the screen an object having the desired screen pixel length. At step 270 of process 200, the object, or series of objects, are displayed at the pixel length, X, determined at step 260, so that the visual angle of a user approximates the desired visual angle, β. As a result of the steps of the process 200 discussed up to this point, the goal of producing objects that appear at a desired size from the perspective of a user equipped with mobile device 120 has been achieved. While the above description shows one manner of obtaining the value of the screen pixel length, X, of the displayed object 310, it is understood that an alternative order of steps or truncation of steps may be taken, as well as alternative approximations be used, without falling outside the scope of the invention. For example, embodiments in which the value for X is derived without separately solving for θ are still considered within the scope of the invention.

According to embodiments in which the displayed objects are optotypes or other eye examination material, step 270 may be part of a vision examination. A variety of different eye tests may be implemented in step 270, depending on the needs of the user. Tests may include: tests of visual acuity; both cylindrical power and spherical power tests; tests for peripheral vision or color blindness; tests for astigmatism, cataracts and various pathologies or diseases, etc. Tests may be static or dynamic. Specific examples of testing material include, without limitation: Snellen charts; E charts; Landoldt C charts, etc.

Figure 6A:
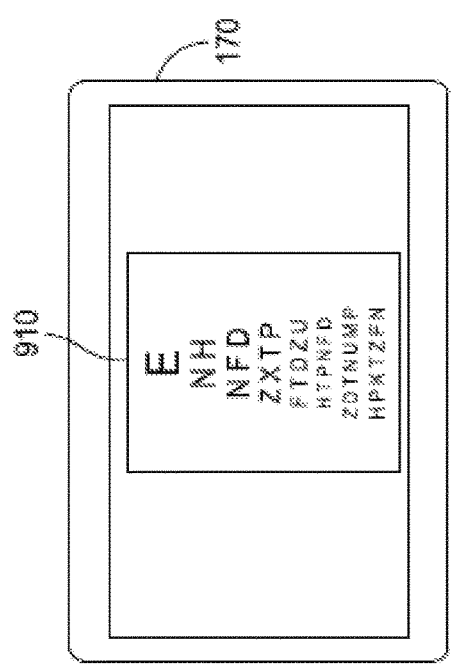
FIGS. 6A and 6B are illustrations of a user interface during a process step according to one or more embodiments.
Figure 6B:
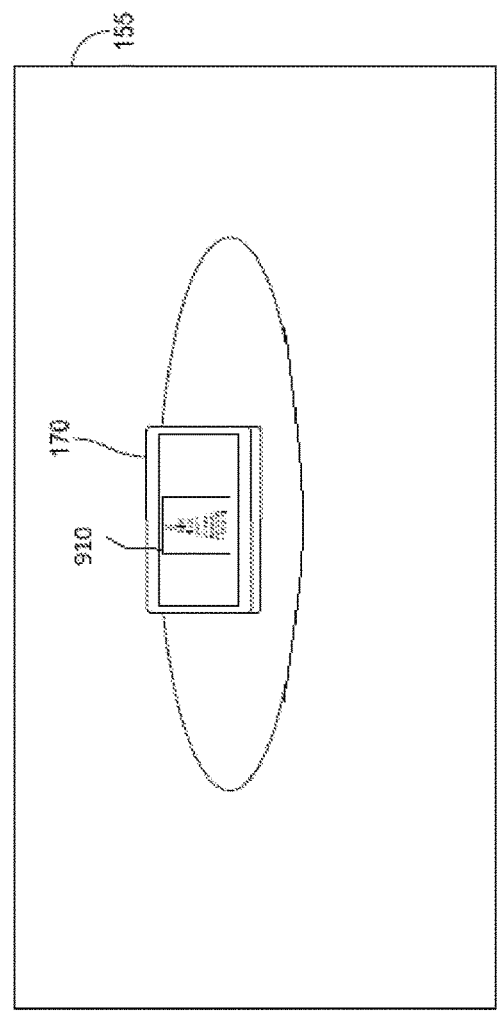

FIGS. 6A and 6B are illustrations of an eye examination, according to one or more embodiments. In FIG. 6A, monitor 170, which is paired with the camera device 120, displays an eye chart 910 in which each of the characters is sized to provide a desired user visual angle. FIG. 6B illustrates a display 155 on the camera device 120.

During testing, at step 280 of process 200 indications are received from the user in response to the displayed eye exam material. The indications may be in the form of vocal or typed responses or any suitable input. The indications may be in response to a prompt provided to the user by one or both of devices 120 and 130. The prompt may include text on one of the screens and/or an audio prompt. The prompt may display or state a command such as "read the second line of characters on the eye chart."

The process 200 may include a step 290 of determining a diagnosis or prescription based on the test subject's indications, or responses. The determination may be conducted automatically by one of the devices 120 and 130 or by the server. The determination may also be done by an optometrist that receives results of the test from the server 110, for example, over the Internet.

As discussed above, aspects and functions disclosed herein may be implemented as hardware or software on one or more of these computer systems. There are many examples of computer systems that are currently in use. These examples include, among others, network appliances, personal computers, workstations, mainframes, networked clients, servers, media servers, application servers, database servers and web servers. Other examples of computer systems may include mobile computing devices, such as cellular phones and personal digital assistants, and network equipment, such as load balancers, routers and switches. Further, aspects may be located on a single computer system or may be distributed among a plurality of computer systems connected to one or more communications networks.

For example, various aspects and functions may be distributed among one or more computer systems configured to provide a service to one or more client computers. Additionally, aspects may be performed on a client-server or multi-tier system that includes components distributed among one or more server systems that perform various functions. Consequently, examples are not limited to executing on any particular system or group of systems. Further, aspects may be implemented in software, hardware or firmware, or any combination thereof. Thus, aspects may be implemented within methods, acts, systems, system elements and components using a variety of hardware and software configurations, and examples are not limited to any particular distributed architecture, network, or communication protocol.

As shown, the computer devices 110, 120, and 130 are interconnected by, and may exchange data through, communication a network 190. The network 190 may include any communication network through which computer systems may exchange data. To exchange data using the network 190, the computer systems 110, 120, and 130 and the network 190 may use various methods, protocols and standards, including, among others, Fibre Channel, Token Ring, Ethernet, Wireless Ethernet, Bluetooth, IP, IPV6, TCP/IP, UDP, DTN, HTTP, FTP, SNMP, SMS, MMS, SS7, JSON, SOAP, CORBA, REST and Web Services. To ensure data transfer is secure, the computer systems 110, 120, and 130 may transmit data via the network 190 using a variety of security measures including, for example, TSL, SSL or VPN.

As discussed above with regard to FIG. 1, various aspects and functions may be implemented as specialized hardware or software executing in one or more computer systems. As illustrated in FIG. 1, the device 120 includes a processor 150, a memory 165, a camera 145, an output display 155, a data storage module 167, and an input device 160. (The following detailed description of the components of mobile device 120, may be generally understood to also apply to corresponding structure present in computer 130 or server 110.)

The processor 150 may perform a series of instructions that result in manipulated data. The processor 150 may be a commercially available processor such as an Intel Xeon, Itanium, Core, Celeron, Pentium, AMD Opteron, Sun Ultra-SPARC, IBM Power5+, or IBM mainframe chip, but may be any type of processor, multiprocessor or controller. The processor 150 is connected to other system elements, including one or more memory devices 165, the camera 145, etc.

The memory 165 may be used for storing programs and data during operation of the device 120. Thus, the memory 165 may be a relatively high performance, volatile, random access memory such as a dynamic random access memory (DRAM) or static memory (SRAM). However, the memory 165 may include any device for storing data, such as a disk drive or other non-volatile storage device. Various examples may organize the memory 165 into particularized and, in some cases, unique structures to perform the functions disclosed herein.

The mobile device 120 also includes one or more interface devices such as input devices 160 and output devices 155. Interface devices may receive input or provide output. More particularly, output devices may render information for external presentation. Input devices may accept information from external sources. Examples of interface devices include keyboards, mouse devices, trackballs, microphones, touch screens, printing devices, display screens, speakers, network interface cards, etc. Interface devices allow the computer system 120 to exchange information and communicate with external entities, such as users and other systems.

The data storage 167 may include a computer readable and writeable nonvolatile (non-transitory) data storage medium in which instructions are stored that define a program that may be executed by the processor 150. The data storage 167 also may include information that is recorded, on or in, the medium, and this information may be processed by the processor 150 during execution of the program. More specifically, the information may be stored in one or more data structures specifically configured to conserve storage space or increase data exchange performance. The instructions may be persistently stored as encoded signals, and the instructions may cause the processor 150 to perform any of the functions described herein. The medium may, for example, be optical disk, magnetic disk or flash memory, among others. In operation, the processor 150 or some other controller may cause data to be read from the nonvolatile recording medium into another memory, such as the memory 165, that allows for faster access to the information by the processor 150 than does the storage medium included in the data storage 167. The memory may be located in the data storage 167 or in the memory 165, however, the processor 150 may manipulate the data within the memory 165, and then copy the data to the storage medium associated with the data storage 167 after processing is completed. A variety of components may manage data movement between the storage medium and other memory elements and examples are not limited to particular data management components. Further, examples are not limited to a particular memory system or data storage system.

Although the device 120 is shown by way of example as one type of a computer device upon which various aspects and functions may be practiced, aspects are not limited to being implemented on the device 120 as shown in FIG. 1. Various aspects and functions may be practiced on one or more computers having a different architectures or components than that shown in FIG. 1. For instance, the device 120 may include specially programmed, special-purpose hardware, such as for example, an application-specific integrated circuit (ASIC) tailored to perform a particular operation disclosed herein. While another example may perform the same function using a grid of several general-purpose computing devices running MAC OS System X with Motorola PowerPC processors and several specialized computing devices running proprietary hardware and operating systems.

The device 120 may include an operating system that manages at least a portion of the hardware elements included in the device 120. Usually, a processor or controller, such as the processor 150, executes an operating system which may be, for example, a Windows-based operating system, such as, Windows NT, Windows 2000 (Windows ME), Windows XP, Windows Vista or Windows 7 operating systems, available from the Microsoft Corporation, a MAC OS System X operating system available from Apple Computer, one of many Linux-based operating system distributions, for example, the Enterprise Linux operating system available from Red Hat Inc., a Solaris operating system available from Sun Microsystems, or a UNIX operating systems available from various sources. Many other operating systems may be used, and examples are not limited to any particular implementation.

The processor 150 and operating system together define a computer platform for which application programs in high-level programming languages may be written. These component applications may be executable, intermediate, bytecode or interpreted code which communicates over a communication network, for example, the Internet, using a communication protocol, for example, TCP/IP. Similarly, aspects may be implemented using an object-oriented programming language, such as .Net, SmallTalk, Java, C++, Ada, or C# (C-Sharp). Other object-oriented programming languages may also be used. Alternatively, functional, scripting, or logical programming languages may be used.

Additionally, various aspects and functions may be implemented in a non-programmed environment, for example, documents created in HTML, XML or other format that, when viewed in a window of a browser program, render aspects of a graphical-user interface or perform other functions. Further, various examples may be implemented as programmed or non-programmed elements, or any combination thereof. For example, a web page may be implemented using HTML while a data object called from within the web page may be written in C++. Thus, the examples are not limited to a specific programming language and any suitable programming language could be used. Thus, functional components disclosed herein may include a wide variety of elements, e.g. executable code, data structures or objects, configured to perform described functions.

Embodiments described above utilize a process for displaying objects on a screen at a desired visual angle in conjunction with the performance of an eye exam. Other embodiments may be used to object display size for a number of different applications including: gaming, educational software, training software, media display, etc. Having thus described several aspects of at least one example, it is to be appreciated that various alterations, modifications, and improvements will readily occur to those skilled in the art. For instance, examples disclosed herein may also be used in other contexts. Such alterations, modifications, and improvements are intended to be part of this disclosure, and are intended to be within the scope of the examples discussed herein. Accordingly, the foregoing description and drawings are by way of example only.

The invention claimed is:

1. A system in communication with a first device capable of receiving input from a camera attached to the first device, and a second device capable of displaying output, the system configured to:
   pair a first device to a second device through an identifier;
   receive, from the first device, data relating to characteristics of a camera operably coupled to the first device and relating to characteristics of an image obtained by the camera of a display device operably coupled to the second device;
   determine a screen pixel length of the display device; and
   transmit instructions to the second device to output for display at the display device an object at a desired visual angle in response to the data received from the second device and the screen pixel length, while the first device is positioned at an arbitrary distance from the screen.

2. The system of claim 1, further configured to receive from the second device an indication of the screen pixel length of the display device.

3. The system of claim 1, wherein the data relating to characteristics of the camera comprise a focal length and a sensor size of the camera.

4. The system of claim 3, wherein the data relating to characteristics of the image obtained by the camera of the display device comprise a camera pixel height of the image and a camera pixel height of the display device within the image.

5. The system of claim 4, wherein the system is further configured to determine a visual angle of the display device prior to transmitting the instructions to the second device to output for display at the display device the object.

6. The system of claim 1, wherein the object displayed at the display device is an optotype, and wherein the system is further configured to receive an indication from one of: the first device or the second device of user input from a test subject proximate to the first device in response to the displayed optotype.

7. The system of claim 6, wherein the system is further configured to determine, based at least in part on the indication of the user input provided by the test subject in response to the optotype displayed at the display device, at least one of: a diagnosis for the test subject, a lens prescription for the test subject, or information to be provided to a doctor to determine a diagnosis or a lens prescription for the test subject.

8. A method for conducting a vision test, comprising:
pairing a first device to a second device through an identifier;
receiving, by a system from the first device, data relating to characteristics of a camera operably coupled to the first device and relating to characteristics of an image obtained by the camera of a display device operably coupled to the second device;
determining, by the system, a screen pixel length of the display device; and
transmitting, by the system, instructions to the second device to output for display at the display device an object at a desired visual angle in response to the data received from the second device and the screen pixel length, while the first device is positioned at an arbitrary distance from the screen.

9. The method of claim 8, further comprising:
receiving, by the system from the second device, an indication of the screen pixel length of the display device.

10. The method of claim 8, wherein the data relating to characteristics of the camera comprise a focal length and a sensor size of the camera.

11. The method of claim 10, wherein the data relating to characteristics of the image obtained by the camera of the display device comprise a camera pixel height of the image and a camera pixel height of the display device within the image.

12. The method of claim 11, further comprising:
determining, by the system, a visual angle of the display device prior to transmitting the instructions to the second device to output for display at the display device the object.

13. The method of claim 8, wherein the object displayed at the display device is an optotype, further comprising:
receiving, by the system, an indication from one of: the first device or the second device of user input from a test subject proximate to the first device in response to the displayed optotype.

14. The method of claim 13, further comprising:
determining, by the system based at least in part on the indication of the user input provided by the test subject in response to the optotype displayed at the display device, at least one of: a diagnosis for the test subject, a lens prescription for the test subject, or information to be provided to a doctor to determine a diagnosis or a lens prescription for the test subject.

15. A non-transitory machine-readable storage medium comprising machine-readable instructions for causing a processor to execute a method for conducting a vision test, comprising:
pairing a first device to a second device through an identifier;
receiving, from the first device, data relating to characteristics of a camera operably coupled to the first device and relating to characteristics of an image obtained by the camera of a display device operably coupled to the second device;
determining a screen pixel length of the display device; and
transmitting instructions to the second device to output for display at the display device an object at a desired visual angle in response to the data received from the second device and the screen pixel length, while the first device is positioned at an arbitrary distance from the screen.

16. The non-transitory machine-readable storage medium of claim 15, wherein the data relating to characteristics of the camera comprise a focal length and a sensor size of the camera.

17. The non-transitory machine-readable storage medium of claim 16, wherein the data relating to characteristics of the image obtained by the camera of the display device comprise a camera pixel height of the image and a camera pixel height of the display device within the image.

18. The non-transitory machine-readable storage medium of claim 17, wherein the object displayed at the display device is an optotype, and wherein the system is further configured to receive an indication from one of: the first device or the second device of user input from a test subject proximate to the first device in response to the displayed optotype.

* * * * *